United States Patent [19]

Huscroft et al.

[11] Patent Number: 5,563,161

[45] Date of Patent: Oct. 8, 1996

[54] ALCOHOLS AND ETHERS WITH AROMATIC SUBSTITUENTS AS TACHYKININ-ANTAGONISTS

[75] Inventors: Ian T. Huscroft, Bishops Stortford; Graeme I. Stevenson, Staffron Walden; Brain J. Williams, Great Dunmow, all of United Kingdom

[73] Assignee: Merck Sharp & Dohme Ltd., Hoddesdon, England

[21] Appl. No.: 397,224

[22] PCT Filed: Sep. 3, 1993

[86] PCT No.: PCT/GB93/01863

§ 371 Date: Mar. 10, 1995

§ 102(e) Date: Mar. 10, 1995

[87] PCT Pub. No.: WO94/15625

PCT Pub. Date: Mar. 17, 1994

[30] Foreign Application Priority Data

Sep. 10, 1992 [GB] United Kingdom .................. 9219175
Nov. 13, 1992 [GB] United Kingdom .................. 9223793

[51] Int. Cl.⁶ .................. C07D 213/40; C07C 235/06; A61K 31/44; A61K 31/085
[52] U.S. Cl. .................. 514/357; 546/336; 560/9; 560/60; 562/470; 564/162; 564/182; 568/55; 568/442; 568/659; 558/410; 514/520; 514/546; 514/557; 514/617
[58] Field of Search .................. 546/336; 560/9, 560/60; 562/470; 564/162, 182; 568/55, 442, 659; 558/410; 514/357, 546, 520, 557, 617, 618, 693, 712, 717, 721, 702

[56] References Cited

U.S. PATENT DOCUMENTS 3,960,960  6/1976  Hollinger et al. .................. 260/570 R

FOREIGN PATENT DOCUMENTS

0394989A2  10/1990  European Pat. Off. .
0436334A2  7/1991  European Pat. Off. .
1448437  9/1976  United Kingdom .

OTHER PUBLICATIONS

Mar., Advanced Organic Chemistry, Third Edition, 1985, pp. 342–343.

"A New and Simple Synthesis of Alkoxy-and Aryloxymethyllithium Reagents (ROCH₂ Li)", E. J. Corey and T. M. Eckrich, Tetrahedron Letters, (1983), vol. 24, No. 31, pp. 3163–3164.

"Trimethylsilyl Chloride–Tin(II) Chloride–Anisole: A Novel Selective p–Methoxybenzyl Ether Cleavage Reagent", T. Akiyama, et al., Synlett, (May 1992), No. 5, pp. 415–416.

Primary Examiner—Zinna Northington Davis
Attorney, Agent, or Firm—Robert J. North; Melvin Winokur

[57] ABSTRACT

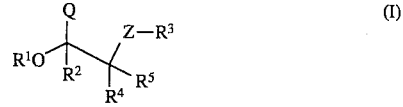

Compounds of formula (I), and salt and prodrugs thereof, wherein Q is optionally substituted phenyl or benzhydryl; $R^1$ is H; optionally substituted $C_{1-6}$alkyl; optionally substituted phenyl($C_{1-4}$alkyl); $C_{2-6}$alkenyl; $C_{2-6}$alkynyl; $COR^a$; $COOR^a$; COHet; $COC_{1-6}$alkylhalo; $COC_{1-6}$alkyl$NR^aR^b$; $CONR^{12}C_{1-6}$alkyl$CONR^aR^b$; $CONR^aR^b$; or $SO_2R^a$; $R^2$ represents H, $C_{1-6}$alkyl or $C_{2-6}$alkenyl; or $R^1$ and $R^2$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$alkyl; $R^3$ is $C_{1-3}$alkyl substituted by optionally substituted phenyl; $R^4$ and $R^5$ are each H, $C_{1-6}$alkyl or $C_{2-6}$alkenyl; and Z represents O or S; are tachykinin receptor antagonists useful in therapy.

14 Claims, No Drawings

ALCOHOLS AND ETHERS WITH AROMATIC SUBSTITUENTS AS TACHYKININ-ANTAGONISTS

This application is a 371 application of PCT/GB/01863 filed Sep. 9, 1993.

This invention relates to a class of azabicyclic compounds, which are useful as tachykinin antagonists. More particularly, the compounds of the invention comprise an aromatic moiety and an hydroxy or alkoxy moiety.

The tachykinins are a group of naturally-occurring peptides found widely distributed throughout mammalian tissues, both within the central nervous system and in the peripheral nervous and circulatory systems. The three known mammalian tachykinins are: substance P, neurokinin A and neurokinin B:

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitus, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

We have now found a class of non-peptides which are potent antagonists of tachykinins.

GB1377350 discloses compounds of formula (A):

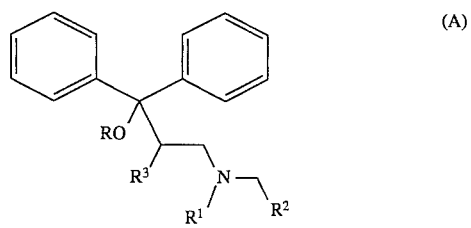

wherein:

R is $C_{1-4}$alkyl;

$R^1$ is H, $C_{1-4}$alkyl, alkyl or benzyl;

$R^2$ is inter alia aralkenyl; and $R^3$ is H or methyl.

The compounds are said to have analgesic and morphine-antagonistic actions.

GB 1443441 and GB 1448437 discloses compounds of formula (B):

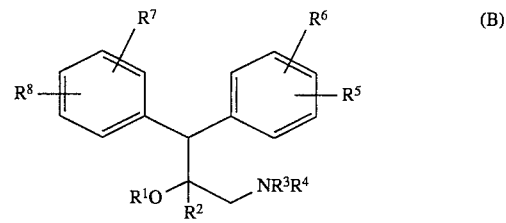

wherein:

$R^1$ is H, $R^9$ or $COR^9$, where $R^9$ is phenyl, benzyl or $C_{1-6}$alkyl optionally substituted by $NR^{10}R^{11}$;

$R^2$ and $R^4$ are each H, methyl or ethyl; and $R^3$ is H, methyl, ethyl or benzyl.

The compounds are said to be useful in the treatment of depression.

E. J. Corey and T. M. Eckrich in *Tetrahedron Letters*, vol. 24, No. 31, pp. 3163–3164 (1983) disclose the preparation of the compound 1-hydroxy-1-phenyl-2-benzyloxyethane from the reaction of bromomethyl benzyl ether with benzaldehyde in the presence of n-butyllithium.

T. Akiyama et al in *Synlett*, No. 5, pp. 415–416 (May 1992) disclose the compound 1-hydroxy-1-phenyl-2-(4-methoxyphenylmethyl)oxyethane as an example of a benzyl ether which may be selectively cleaved by trimethylsilyl chloride-tin(II) chloride-anisole to yield 1-phenylethane-1,2-diol.

The present invention provides a compound of formula (I), or a salt or prodrug thereof:

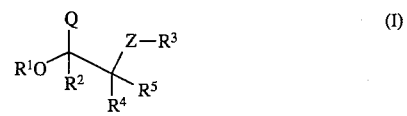

wherein

Q represents optionally substituted phenyl or optionally substituted benzhydryl;

$R^1$ represents: H;

$C_{1-6}$alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$; Het; COHet; $CONR^{12}C_{1-6}$alkylHet; $CONR^{12}C_{1-6}$alkyl$CONR^aR^b$ or $NR^aR^b$;

phenyl($C_{1-4}$alkyl) (optionally substituted by one or more of $C_{1-6}$alkyl, $C_{1-6}$alkoxy, halo and trifluoromethyl in the phenyl ring);

$C_{2-6}$alkenyl;

$C_{2-6}$alkynyl;
$COR^a$;
$COOR^a$;
COHet;
$COC_{1-6}$alkylhalo;
$COC_{1-6}$alkyl$NR^aR^b$;
$CONR^{12}C_{1-6}$alkyl$CONR^aR^b$;
$CONR^aR^b$; or
$SO_2R^a$;

$R^2$ represents H, $C_{1-6}$alkyl or $C_{2-6}$alkenyl;

or $R^1$ and $R^2$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$alkyl;

$R^3$ represents $C_{1-3}$alkyl substituted by a phenyl group which may itself optionally be substituted by one or more of $C_{1-6}$alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ and $CONR^cR^d$;

$R^4$ and $R^5$ each represent H, $C_{1-6}$alkyl or $C_{2-6}$alkenyl;

Z represents O or S;

$R^{12}$ represents H, $C_{1-6}$alkyl, phenyl (optionally substituted by one or more of $C_{1-6}$alkyl, $C_{1-6}$alkoxy, halo and trifluoromethyl) or phenyl($C_{1-4}$alkyl) (optionally substituted in the phenyl ring by one or more of $C_{1-6}$alkyl, $C_{1-6}$alkoxy, halo and trifluoromethyl);

$R^a$ and $R^b$ each independently represent H, $C_{1-6}$ alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$alkyl, $C_{1-6}$alkoxy, halo and trifluoromethyl) or $R^a$ and $R^b$ together form a chain $(CH_2)_p$ optionally substituted by oxo where p is 4 or 5 and where one methylene group may optionally be replaced by an oxygen atom or a group $NR^x$, where $R^x$ is H or $C_{1-6}$ alkyl;

$R^c$ and $R^d$ independently represent H, $C_{1-6}$alkyl, phenyl or trifluoromethyl; and Het represents an aromatic heterocycle optionally substituted by $C_{1-6}$alkyl, $C_{1-6}$alkoxy, oxo, thioxo, halo, trifluoromethyl, $NR^aR^b$, $NR^aCOR^b$, $CONR^aR^b$, $CO_2R^a$, $SR^a$, $SO_2R^a$ or $CH_2OR^a$, where $R^a$ and $R^b$ are as above defined.

As used herein, the definition of each expression, when it occurs more than once in any structure, is intended to be independent of its definition elsewhere in the same structure.

The alkyl, alkenyl and alkynyl groups referred to with respect to any of the formulae herein may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

For phenylalkyl substituents, the alkyl moiety may be straight or branched.

The term "halo" as used herein includes fluoro, chloro, bromo and iodo.

Where Q represents substituted phenyl or benzhydryl, suitable substituents include $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^a$-$COOR^b$, $COOR^a$ or $CONR^aR^b$, where $R^a$ and $R^b$ are as above defined. One or more substituents may be present and each may be located at any available ring position.

Suitably Het represents an optionally substituted heteroaryl moiety selected from thienyl, furyl, pyrrolyl, pyridyl, pyrazolyl, triazolyl, tetrazolyl, thiazolyl, pyrazinyl, pyrimidinyl, pyridazinyl, oxazolyl, triazinyl, oxadiazolyl, thiadiazolyl, isoxazolyl, quinolyl, isothiazolyl, imidazolyl, benzimidazolyl, benzoxazolyl, benzothiophenyl, benzofuranyl and indolyl.

A subgroup of compounds of the present invention is represented by compound of formula (IA), and salts and prodrugs thereof:

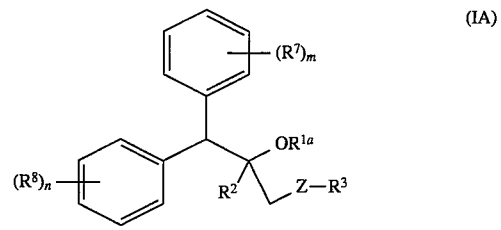

(IA)

wherein

Z, $R^2$ and $R^3$ are as defined for formula (I) above;

$R^{1a}$ represents H or $C_{1-6}$alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$, $CONR^{12}C_{1-6}$alkyl$CONR^aR^b$ or $NR^aR^b$ (where $R^a$, $R^b$ and $R^{12}$ are as defined for formula (I) above); phenyl($C_{1-4}$alkyl) (optionally substituted by one or more of $C_{1-6}$alkyl, $C_{1-6}$alkoxy, halo and trifluoromethyl in the phenyl ring); $C_{2-6}$alkenyl; $C_{2-6}$ alkynyl; $COR^a$; $COOR^a$; $COC_{1-6}$alkylhalo; $COC_{1-6}$alkyl$NR^aR^b$; $CONR^{12}C_{1-6}$alkyl$CONR^aR^b$; $CONR^aR^b$; or $SO_2R^a$; or $R^1$ and $R^2$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$ alkyl;

each $R^7$ independently represents $C_{1-6}$alkyl, $C_{1-6}$alkoxy, halo or trifluoromethyl;

each $R^8$ independently represents $C_{1-6}$alkyl, $C_{1-6}$alkoxy, halo or trifluoromethyl; and n and m each represent 0, 1, 2 or 3.

A second subgroup of compounds of the present invention is represented by compounds of formula (IB), and salts and produgs thereof:

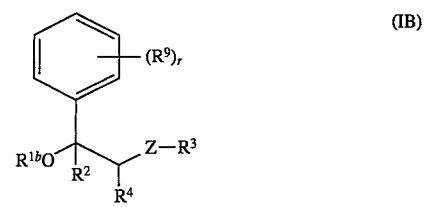

(IB)

wherein Z, $R^3$ and $R^4$ are as defined for formula (I) above;

$R^{1b}$ represents: H;

$C_{1-6}$alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$, Het; COHet; $CONR^{12}C_{1-6}$alkyl$CONR^aR^b$ or $NR^aR^b$;

phenyl($C_{1-4}$alkyl) (optionally substituted by one or more of $C_{1-6}$alkyl, $C_{1-6}$ alkoxy, halo and trifluoromethyl in the phenyl ring);

$C_{2-6}$ alkenyl;

$C_{2-6}$ alkynyl;
$COR^a$;
$COOR^a$;
COHet;
$COC_{1-6}$alkylhalo;
$COC_{1-6}$alkyl$NR^aR^b$;
$CONR^{12}C_{1-6}$alkyl$CONR^aR^b$;
$CONR^aR^b$; or
$SO_2R^a$;

where $R^a$, $R^b$ and $R^{12}$ are as defined for formula (I) above;

$R^2$ represents H, $C_{1-6}$alkyl or $C_{2-6}$alkenyl;

each $R^9$ independently represents $C_{1-6}$alkyl, $C_{1-6}$alkoxy, halo or trifluoromethyl;

r represents 0, 1, 2 or 3; and

Het represents an aromatic heterocycle optionally substituted by $C_{1-6}$alkyl, $C_{1-6}$alkoxy, oxo, thioxo, halo, trifluoromethyl, $NR^aR^b$, $NR^aCOR^b$, $CONR^aR^b$, $CO_2R^a$, $SR^a$, $SO_2R^a$ or $CH_2OR^a$, where $R^a$ and $R^b$ are as above defined.

One subgroup of compounds according to the invention is represented by compounds of formula (I) wherein Q is optionally substituted benzhydryl.

A further subgroup of compounds according to the invention is represented by compounds of formula (I) wherein Q is optionally substituted phenyl.

In the compounds of formula (I) it is preferred that Q is unsubstituted phenyl or unsubstituted benzhydryl.

Preferably $R^1$ represents H or substituted $C_{1-6}$alkyl, more preferably $CH_2$ substituted by a group $CONR^aR^b$, such as $CONH_2$, $COOR^a$, such as $COOCH_3$, or $CONR^{12}C_{1-6}$alkyl-Het, such as $CONR^{12}CH_2$Het, in particular $CONR^{12}CH_2$pyridyl. More preferably $R^1$ represents $CH_2CONR^aR^b$ or $CH_2CONR^{12}C_{1-6}$alkylHet. Another suitable value for $R^1$ is $C_{1-6}$alkyl substituted by Het such as optionally substituted triazolyl, thiazolyl, oxadiazolyl or imidazolyl.

Suitable values for the groups $R^2$, $R^4$ and $R^5$ include H and methyl, preferably H.

Suitably $R^3$ represents a $C_{1-3}$alkyl, such as $CH_2$ $CH(CH_3)$ or $C(CH_3)_2$, bearing a substituent which is a substituted phenyl group. Suitable phenyl substituents include $C_{1-6}$alkyl such as i-butyl, t-butyl, i-propyl, cyclopropyl, ethyl and especially methyl, $C_{1-6}$alkoxy such as i-propoxy, ethoxy, and especially methoxy, phenoxy, nitro, cyano, halo such as bromo, chloro, fluoro and iodo, and trifluoromethyl. Preferably $R^3$ represents $CH_2$ substituted by a substituted phenyl group. Preferably one or two substituents selected from $C_{1-4}$alkyl, such as methyl and t-butyl, $C_{1-4}$alkoxy, such as methoxy, trifluoromethyl and halo such as bromo, chloro, fluoro and iodo will be present in the phenyl ring. More preferably $R^3$ represents $CH_2$ substituted by 3,5-disubstituted phenyl, such as 3,5-dimethylphenyl or 3,5-bistrifluoromethylphenyl.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The present invention includes within its scope solvates of the compounds of formula (I) and salts thereof, for example, hydrates.

The compounds according to the invention have at least one asymmetric centre, and may accordingly exist both as enantiomers and as diastereoisomers. It is to be understood that all such isomers and mixtures thereof are encompassed within the scope of the present invention.

The substance P antagonising activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of the Examples were found to have $IC_{50}$ values less than 200 nM.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; small cell carcinoma such as small cell lung cancer; respiratory diseases such as chronic obstructive airways disease, bronchopneumonia, bronchospasm and asthma; inflammatory diseases such as inflammatory bowel disease, irritable bowel syndrome, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like, and proliferative vitreoretinopathy; cutaneous diseases such as contact dermatitis, atropic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as cystitis and bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0..05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention may be prepared by reaction of compounds of formula (II) with compounds of formula (III)

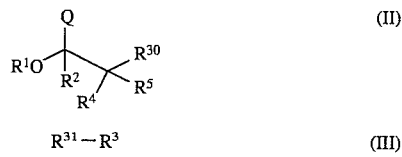

(II)

$$R^{31} - R^3$$ (III)

wherein Q, $R^2$, $R^3$ $R^4$ and $R^5$ are as defined for formula (I), $R^1$ is as defined for formula (I) except that, when $R^1$ is H it is replaced by a suitable protecting group, such as tetrahydropyranyl; and one of $R^{30}$ and $R^{31}$ represents a leaving group and the other of $R^{30}$ and $R^{31}$ represents ZH, where Z is as defined for formula (I); in the presence of a base, followed by deprotection, if required.

Suitably $R^{30}$ represents ZH and $R^{31}$ represents a leaving group.

Suitable leaving groups include halo, e.g. chloro, bromo or iodo, or sulphonate derivatives such as tosylate or mesylate.

The reaction is conveniently carried out in a suitable organic solvent, such as dimethylformamide, at a temperature in the region of 0° C. Favoured bases of use in the reaction include alkali metal hydrides, such as sodium hydride.

Alternatively, compounds of formula (I) wherein $R^1$ is H and $R^2$ is H may b6 prepared by reduction of compounds of formula (IV):

(IV)

wherein Q, $R^3$, $R^4$, $R^5$ and Z are as defined for formula (I).

Suitable reducing agents of use in the reaction include hydride reducing agents, such as, for example, sodium borohydride.

The reaction is conveniently effected in a suitable organic solvent, such as an alcohol, e.g. methanol, suitably at room temperature.

Compounds of formula (I) where $R^2$ is other than H may be prepared from compounds of formula (II) by reaction with a Grignard reagent of formula $R^2MgHal$, wherein Hal is as previously defined. Suitable reagents and conditions will be readily apparent to those skilled in the art.

Compounds of formula (I) may also be prepared from different compounds of formula (I) by interconversion processes. In particular, interconversion processes may be used to vary the group $R^1$. For example, compounds of formula (I) wherein $R^1$ is other than H may be prepared from the corresponding compounds of formula (I) wherein $R^1$ is H by conventional methods, such as reaction with a compound $R^1$-Hal, where Hal represents halo, in the presence of a base. Suitable reagents and conditions will be readily apparent to those skilled in the art and are illustrated by the accompanying Examples. Suitable bases include organic bases, such as tertiary amines, e.g. triethylamine, and inorganic bases, such as alkali metal carbonates, e.g. sodium carbonate. Compounds of formula (I) wherein $R^1$ is $C_{1-6}$ alkyl substituted by $CONR^aR^b$ may be prepared from corresponding compounds of formula (I) wherein $R^1$ is $C_{1-6}$ alkyl substituted by $CO_2R^a$ by treatment with ammonia or an amine of formula $NR^aR^b$.

The intermediates of formula (II) above wherein $R^{30}$ is SH may be prepared from the corresponding intermediates of formula (II) wherein $R^{30}$ represents OH by treating the latter compound with hydrogen sulphide in the presence of aluminium oxide, as described by Lucien et al., *Nouveau J. Chem.*, 3, 15 (1979), or phosphorus pentasulphide in a suitable solvent, e.g. pyridine, at ambient or elevated temperatures, suitably at reflux temperature.

Intermediates of formula (II) above wherein $R^{30}$ is OH and $R^4$ is H may be prepared from corresponding compounds of formula (V):

(V)

wherein Q, $R^1$ and $R^2$ are as defined for formula (II) and $R^{40}$ represents alkyl, by reduction.

Suitable reducing agents of use in the reaction include metal hydrides, for example, lithium aluminium hydride. The reaction is conveniently effected in a suitable organic solvent, such as an ether, for example, tetrahydrofuran.

Compounds of formula (V) wherein $R^1$ is other than H may be prepared from the corresponding compounds of formula (V) wherein $R^1$ is H by reaction with a reagent suitable to introduce the group $R^1$ as defined for formula (II) using conventional procedures. General methods for introducing the group $R^1$ are discussed above for the preparation of compounds of formula (I). Suitable procedures are described in the Examples and further procedures will be readily apparent to those skilled in the art.

Compounds of formula (V) wherein $R^1$ is H are commercially available or maybe prepared from commercially available starting materials using conventional methods well known to those skilled in the art.

Compounds of formula (II) wherein $R^{30}$ is OH and $R^4$ and/or $R^5$ are other than H may be prepared from intermediates of formula (VI)

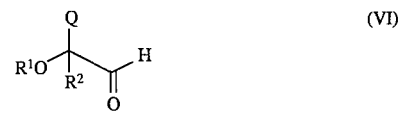

(VI)

wherein Q, $R^1$ and $R^2$ are as defined for formula (II), by reaction with an organometallic reagent of formula $MR^4$ and/or $MR^5$, wherein $R^4$ and $R^5$ are as previously defined and M represents a metal, such as lithium, or a metal halide, such as a magnesium halide, e.g. magnesium chloride or magnesium bromide.

The reaction is suitably effected in an inert organic solvent such as an ether, for example, diethylether or tetrahydrofuran.

Aldehydes of formula (VI) may be prepared by reduction of esters of formula (V) wherein $R^{40}$ is alkyl using diisobutylaluminium hydride.

Compounds of formula (IV) may be prepared by reaction of a compound of formula (VII) with a compound of formula (VIII)

 (VII)

 (VIII)

wherein Q, $R^3$, $R^4$, $R^5$, Z and Hal are as previously defined and $R^{30}$ represents alkyl, such as butyl.

The reaction is preferably effected in the presence of a suitable catalyst, such as palladium (II) catalyst, for example benzylchlorobis(triphenylphosphine) palladium(II), conveniently in a suitable organic solvent, such as a halogenated hydrocarbon, e.g. chloroform, preferably at elevated temperature, such as 60°–100° C.

Alternatively, compounds of formula (IV) may be prepared by reaction of a compound of formula (IX) with a compound of formula (X)

 (IX)

$M^1-Q$ (X)

wherein Q, $R^3$, $R^4$, $R^5$ and Z are as previously defined and $M^1$ represents an alkali metal, such as lithium.

The reaction is conveniently effected in a suitable organic solvent, such as an ether, e.g. diethyl ether. Preferably the reaction is effected at low temperature, such as about –80° C., and the reaction mixture subsequently allowed to reach ambient temperature.

Compounds of formula (VII) may be prepared from the corresponding alcohols of formula $R^3OH$ by reaction with a compound of formula $Hal-CH_2SnR^{30}{}_3$, wherein $R^{30}$ and Hal are as previously defined, in the presence of a base, such as an alkali metal hydride, e.g. sodium hydride.

Compounds of formulae $R^3OH$ and (VIII) are commercially available or may be prepared from commercially available starting materials by conventional methods.

Compounds of formula $Hal-CH_2SnR^{30}{}_3$ are commercially available.

Compounds of formula (IX) may be prepared by reaction of halides of formula $R^3Hal$, wherein $R^3$ and Hal are as previously defined, with cyanohydrin.

Compounds of formula $R^3Hal$ are commercially available or may be prepared from commercially available starting materials by conventional methods.

Intermediates of formula (VI) are conveniently not isolated but generated in situ using a metallating agent, such as a lithiating agent, e.g. n-butyl lithium.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, compounds of formula (I) wherein $R^1$ is H may be resolved into their component enantiomers by standard techniques, such as the formation of diastereomeric esters or amides, followed by chromatographic separation and removal of the chiral auxiliary. These compounds can then be used to make individual enantiomers of compounds of formula (I) wherein $R^1$ is other than H.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

1-(3,5-Bis(trifluoromethyl)phenyl)methyloxy-3,3-diphenyl-2-hydroxypropane a) Preparation of 1-(3.5-bis(trifluoromethyl)phenyl) methyloxy)-3,3-diphenylacetone

Method A i) Sodium hydride (80% suspension in oil, 2.03 g) was washed twice with petroleum ether and to this solid was added tetrahydrofuran (50 ml) and dimethylformamide (3 ml) followed by the slow addition of a solution of 3,5-bis(trifluoromethyl) benzyl alcohol (15 g) in tetrahydrofuran (50 ml). After the effervescence had subsided (30 minutes) a solution of tri-n-butyltinmethylene iodide (25.2 g) was added. The solution was heated to reflux for 2 hours, cooled to room temperature and quenched by careful addition of petroleum ether bp 60°–80° C. (500 ml) and water (200 ml). The organic phase was washed with water and dried ($MgSO_4$). After removal of the solvent in vacuo the residue was distilled under reduced pressure $bp_{0.8}=140°$ C. to give tri-n-butyl-((3,5- bis(trifluoromethyl)phenyl) methyloxymethyl)tin. $^1$H NMR (360MHz, $CDCl_3$) δ7.78 (1H, s, $^{4\text{-}}aryl^{\text{-}}H$), 7.76 (2H, s, $^{2,6\text{-}}aryl^{\text{-}H}$), 4.52 (2H, s, aryl-$CH_2$).

ii) Diphenylacetyl chloride (4.6 g), tri-n-butyl-((3,5-bis-(trifluoromethyl)phenyl)methyloxymethyl)tin (12.6 g; Example 1a, (Method Ai)and benzylchlorobis(triphenylphosphine) palladium (II)(80 mg)were dissolved in chloroform (10 ml) and the solution heated at 80° C. for 6h. On cooling diethyl ether and saturated aqueous potassium fluoride were added and after 30 minutes the solution was filtered through Hiflo™. The organic layer was washed with water, saturated brine and dried ($MgSO_4$). After evaporation in vacuo the residual oil was purified by chromatography on silica gel (eluting with 0 to 10% ethyl acetate in petroleum ether bp=60°–80° C.) to give 1-(3,5-bis(trifluoromethyl)phenyl)methyloxy)-3,3-diphenyl acetone as an oil. $^1$H NMR ($CDCl_3$, 360MHz) δ7.80 (1H; s; 4-aryl $CH$) 7.71 (2H; s; 2,6-aryl CH), 7.43–7.24 (10H; m; phenyl), 5.30 (1H; s; $Ph_2CH$), 4.56 (2H; s), 4.31 (2H; s). m/e Found 452.1191, $C_{24}H_{13}F_6O_2$ requires 452.12110.

Method B i) To a solution of cyanohydrin (70% in water, 20 ml) and powdered $K_2CO_3$ (90.7 g) in ethyl acetate (250 ml) was added 3,5-bis(trifluoromethyl)benzyl bromide (40.3 g). the solution was stirred at room temperature for 15 minutes then was heated to reflux for 2.5 hours. After cooling to room temperature water (500 ml) and ethyl acetate (500 ml) were added and the organic phase washed with saturated brine (2 times) and dried (MgSO$_4$). After removal of the solvent in vacuo the residual oil was distilled under reduced pressure through a 3" vigreux column $^{bp}$1.8=92°–108° to give ((3,5-bis(trifluoromethyl)phenyl) methyloxy)acetonitrile. $^1$H NMR (250MHz, CDCl$_3$) δ7.86 (1H, s), 7.82 (2H, s), 4.85 (2H, s), 4.40 (2H, s).

ii) To a cooled (–80° C.) solution of ((3,5-bis(trifluoromethyl)phenyl)methyloxy)acetonitrile (0.51 g; Example 1a, Method B(i) was added 0.42M lithio diphenylmethane (10 ml; prepared by addition of 2.5M n-butyl lithium in hexane (10 ml) to a cooled (–80° C.) solution of diphenylmethane (4.2 g) in diethyl ether (5 ml), followed by warming to room temperature for 3 hours). The solution was warmed to room temperature for 0.5h and then 1M-hydrochloric acid (10 ml) and ethyl acetate were added and the organic phase washed with saturated brine and dried (MgSO$_4$). After evaporation in vacuo the residue was chromatographed on silica gel (eluting with 5% ethyl acetate in hexane ) to give 1-(3,5-bis(triflouromethyl)phenyl)methyloxy)-3,3-diphenyl acetone as an oil which gave an identical $^1$H NMR spectrum to the material prepared by Method A.

b) 1-(3,5-Bis(trifluoromethyl)phenyl)methyloxy-3,3-diphenyl- 2-hydroxypropane

To a solution of 1-(3,5-bis(trifluoromethyl) phenyl)methyloxy)-3,3-diphenylacetone (Example 1a, 0.252 g) in methanol (10 ml) was added sodium borohydride (0.021 g). After 0.5h the solution was evaporated to dryness and the residue was partitioned between ethyl acetate and 10% aqueous citric acid. The organic phase was washed further with water, saturated brine and dried (MgSO$_4$). After evaporation in vacuo the residue was purified by silica gel chromatography (eluting with 20% ethyl acetate in hexane) to give 1-(3,5-bis (trifluoromethyl)phenyl)methyloxy-3,3-diphenyl-2-hydroxypropane as an oil. $^1$H NMR (360MHz, CDCl$_3$) δ7.79 (1H, s; 4-aryl C$\underline{H}$) 7.41–7.16 (10H; m; phenyl), 4.6 (1H; m; HOC$\underline{H}$) 4.58 (2H; dd Jgem=12.7 Hz; OC$\underline{H}_A$H$_B$ aryl), 4.10 (1H; d, J=9.09 Hz; Ph$_2$C$\underline{H}$), 3.57 (1H; dd J=9.79 Hz, 2.93 Hz; CHC$\underline{H}_A$H$_B$O), 3.45 (1H; dd, J=9.76 Hz, 6.2 Hz; CHCH$_A$$\underline{H}_B$O). Found: C, 63.05; H, 4.54; C$_{24}$H$_{22}$F$_6$O$_2$. 0.1(H$_2$O) requires C, 63.19; H, 4.46%.

EXAMPLE 2

1-((3,5-Bis(trifluoromethyl)phenyl)methyloxy)-2-((carboxamido)methyloxy)-3,3-diphenylpropane a) To a cooled solution (0° C.) of 1-(3,5-bis(trifluoromethyl) phenyl)methyloxy-3,3-diphenyl-2-hydroxypropane (Example 1; 0.49 g) in a mixture of tetrahydrofuran (4 ml) and dimethylformamide (1 ml) was added 80% sodium hydride (0.039 g; suspension in oil). After 0.5 hours methyl bromoacetate (0.121 ml) was added and the solution stirred at room temperature for 16 hours. Water (0 ml) and ethyl acetate (50 ml) were added and the organic phase washed with water (5 times), saturated brine and dried (MgSO$_4$). After removal of the solvent in vacuo the residue was purified by silica gel chromatography (eluting with 10% ethyl acetate in hexane) to give 1-((3,5-bis(trifluoromethyl)phenyl)methyloxy)-2-(carbomethoxy) methyloxy-3,3-diphenylpropane m/e CI$^+$=544 (M+NH$_4^+$).

b) To a cooled solution (0° C.) of the product of Example 2a (0.2 g) in methanol (20 ml) was added ammonia gas until the solution was saturated. The flask was sealed to prevent escape of the ammonia and the solution stored at room temperature for 72 hours. The solution was then evaporated to dryness and the residue purified by chromatography on silica gel (eluting with 50% ethyl acetate in hexane) to give 1-((3,5-bis(trifluoromethyl)phenyl)methyloxy)-2-((carboxamido) methyloxy)-3,3-diphenylpropane as an oil, m/e Found 511.15840 C$_{26}$H$_{23}$F$_6$NO$_3$ requires 511.15821. $^1$H NMR (360MHz, CDCl$_3$) δ7.8 (1H; s; 4-aryl CH), 7.71 (2H; s; 2,6-aryl C$\underline{H}$, 7.4–7.2 (10H; m; aryl), 6.0 (1H, bs; NH$_A$H$_B$), 5.7 (1H; bs; NH$_A$H$_B$), 4.53 (1H; d, Jgem=12.8 Hz), 4.3 (1H; m; OC$\underline{H}$-CH$_2$), 4.17 (1H; d J=9.4 Hz; Ph$_2$C$\underline{H}$), 4.03 (1H; d, Jgem=15.8 Hz), 3.83 (1H; d, Jgem=15.8 Hz) 3.6 (1H; dd, J=10.4 and 2.57 Hz) 3.5 (1H; dd, J=10.4 and 5.52 Hz).

EXAMPLE 3

2-[3,5-Bis(trifluoromethyl)phenyl]methyloxy-1-phenylethanol a) (5)-(+)Methyl mandelate (5.8h) and 3,4-dihydro-2H-pyran (3.3 ml) were dissolved in dry dichloromethane (40 ml) containing pyridinium-p-toluene sulphonate (0.84 g). The mixture was stirred at room temperature for 18 hrs. The reaction mixture was then washed with water (50 ml) and brine (50 ml) and dried (MgSO$_4$). Filtration and removal of solvent under reduced pressure gave (5)-methyl-2-(tetrahydropyranyloxy)phenyl acetate as a clear oil (6.4 g) MS (CI$^+$) 251 (M+H) 268 (M+NH$_4$) (CI$^-$) 249 (M–H).

b) A solution of (5)-methyl-2-(tetrahydropyranyloxy) phenyl acetate (6.4 g) in dry tetrahydrofuran (10 ml) was added dropwise to a solution of lithium aluminium hydride (12.6 ml, 1.0M) in dry tetrahydrofuran at 0° C. The reaction was allowed to proceed for 1 hr and was then quenched by addition of 4N sodium hydroxide solution. The mixture was filtered and the filtrate extracted into ethyl acetate, dried (MgSO$_4$), filtered and the solvent removed under reduced pressure to afford a clear oil. The recovered oil was dissolved in dry dimethylformamide (20 ml) and treated with sodium hydride (0.8 g, 60%). The mixture was stirred at room temperature for 25rains and then treated with 3,5-bis(trifluoromethyl)benzyl bromide (3.6 ml). The reaction was allowed to stir at room temperature for 18 hrs, quenched by the addition of water (200 ml), and extracted into ethyl acetate (100 ml). The organic layer was evaporated, and washed with water (200 ml), brine (100 ml), dried (MgSO$_4$), filtered and the solvent removed under reduced pressure to give a yellow oil. Purified by flash chromatography on silica gel (EtOAc/nHex 1:19) afforded a clear oil (4.0 g) which was dissolved in a solution of 10% 3NHCl in methanol (20 ml). The reaction was stirred at room temperature for 1 hr at which time no starting material would be detected. Solvent was removed and reduced pressure and the residue partitioned between ethyl acetate and water. The organic layer was separated dried (MgSO$_4$), filtered and the solvent removed under reduced pressure to afford the product as a clear oil. $^1$H NMR (360MHz, CDCl$_3$) δ3.63 (1H, dd, J=8.5 and 1.0 Hz), 3.71 ( 1H, dd, J=3.5 and 1.0 Hz), 4.64 (2H, s), 5.0 (1H, dd, J=3.5 and 1.0 Hz), 7.22–7.40 (5H, m), 7.78 (2H, s), 7.84 (1H, s). MS (CI$^+$) 382 [M+NH$_4$]; C$_{17}$H$_{14}$O$_2$F$_6$ requires C, 56.65; H, 3.87. Found C, 55.86; H, 3.91%

EXAMPLE 4

1-(3,5-Bis(trifluoromethyl)phenyl)methyloxy-2-[N-methyl-N-(3-pyridylmethyl)acetamidomethyloxy]-2-phenylethane hydrochloride salt Sodium hydride (110 mg, 60%) was added to a stirred suspension of the compound of Example 3 (500 mg) and 3-N-methyl( chloroacetamidomethyl)pyridine hydrochloride (320mg) in dry dimethylformamide (8.0 ml). The mixture was warmed to 60° C. for 2 hrs, then cooled to room temperature and poured into water (100 ml), and extracted into ethyl acetate. The organic layers were separated and washed with water (100 ml), brine (50 ml), dried (MgSO$_4$), filtered and the solvent removed under reduced pressure to afford a brown oil. Purified by flash chromatography on silica gel (EtOAc). The purified product was dissolved in dry ether (10 ml) and treated with a saturated solution of HCl in ether to give a white precipitate. Recrystallisation from ether gave the product as white needles. mp. 123° C. $^1$H NMR (360MHz, DMSO) δ2.8 (1H, s), 2.95 (3H, s), 3.60–3.84 (2H, m), 4.23 (2H, q, J=7.0 Hz), 4.64 (2H, s), 4.72 (2H, s), 7.14–7.21 (4H, m), 7.84 (1H, s), 7.90 (2H, s), 7.92 (1H, s), 8.04 (1H, m), 8.41 (1H, m), 8.82 (2H, m). C$_{26}$H$_{24}$F$_6$N$_2$O$_3$HCl.0.25H$_2$O requires C, 55.03; H, 4.53; N, 4.94. Found C, 55.05; H, 4.52; N, 4.79%.

EXAMPLE 5

1-(3,5-Bis(trifluoromethyl)phenyl)methyloxy-2-carbomethoxymethyloxy-2-phenylethane Sodium hydride (25 mg, 60%) was added to a stirred solution of methylbromoacetate (84 mg) and the compound of Example 3 (200 mg) in dry dimethylformamide (0.5 ml). The mixture was stirred at 23° C. for 18 hrs, then partitioned between water and ethyl acetate. The organic layer was separated, dried (MgSO$_4$), filtered and concentrated in vacuo. The residue was purified by flash column chromatography on silica gel eluting with 9:1 hexanes:ethyl acetate to give the title compound as a clear oil. $^1$H NMR (250MHz, CDCl$_3$) δ3.60–3.68 (1H, m), 3.68 (3H, s), 3.80–3.94 (1H, m), 3.95–4.21 (2H, q), 4.64–4.80 (3H, m), 7.23–7.39 (5H, m), 7.80 (3H, s).

EXAMPLE 6

1-(3,5-Bis(trifluoromethyl)phenyl)methyloxy-2-N-methylcarboxamidomethyloxy-2-phenylethane Anhydrous methylamine gas was bubbled through a solution of the compound of Example 5 (200 mg) for 10 minutes. The solution was then transferred to a thick-walled sealed flask and stored at 4° C. for 18 hrs. The mixture was cooled to −78° C. before opening, then concentrated in vacuo. Residue was purified by flash column chromatography on silica gel eluting with 1:1, hexanes:ethyl acetate to give the title compound as a clear oil. $^1$H NMR (360MHz, CDCl$_3$) δ2.71 (3H, d, J=4.9 Hz), 3.63–3.66 (1H, dd, J=3.1 Hz), 3.75–3.83 (2H, m), 4.01–4.05 (1H, d, 16 Hz), 4.53–4.59 (1H, dd, J=3.0 Hz), 4.70 (2H, s), 7–7.72 (1H, b), 7.31–7.40 (5H, m), 7.81 (2H, s), 7.84 (1H, s). MS (CI$^+$) 436 [M], 453 [M+NH$_4$]. C$_{20}$H$_{19}$F$_6$NO$_3$ requires C, 55.18; H, 4.40; N, 3.22. Found C, 55.27; H, 4.47; N, 3.11.

The following examples illustrate pharmaceutical compositions according to the invention.

EXAMPLE 7A

Tablets containing 1–25 mg of compound

| | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 7B

Tablets containing 26–100 mg of compound

| | Amount mg | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 8

Parenteral injection

| | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 9

Topical formulation

| | Amount mg |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

We claim:

1. A compound of formula (I), or a pharmaceutically acceptable salt or prodrug thereof:

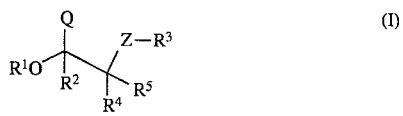

(I)

wherein

Q represents optionally substituted phenyl or optionally substituted benzhydryl;

$R^1$ represents: H;

$C_{1-6}$alkyl optionally substituted by hydroxy, cyano, $COR^a$, $COOR^a$, $CONR^aR^b$, $COC_{1-6}$alkylNR$^a$R$^b$, $CONR^{12}C_{1-6}$alkylOR$^a$; Het; COHet; $CONR^{12}C_{1-6}$alkylHet; $CONR^{12}C_{1-6}$alkylCONR$^a$R$^b$ or NR$^a$R$^b$;

phenyl($C_{1-4}$alkyl) (optionally substituted by one or more of $C_{1-6}$alkyl, $C_{1-6}$alkoxy, halo and trifluoromethyl in the phenyl ring);

$C_{2-6}$alkenyl;

$C_{2-6}$alkynyl;

$COR^a$;

$COOR^a$;

COHet;

$COC_{1-6}$alkylhalo;

$COC_{1-6}$alkylNR$^a$R$^b$;

$CONR^{12}C_{1-6}$alkylCONR$^a$R$^b$;

$CONR^aR^b$; or $SO_2R^a$;

$R^2$ represents H, $C_{1-6}$alkyl or $C_{2-6}$alkenyl;

or $R^1$ and $R^2$ together form a chain $(CH_2)_q$ optionally substituted by oxo where q is 4 or 5 and where one methylene group may optionally be replaced by an oxygen atom or a group NR$^x$, where R$^x$ is H or $C_{1-6}$alkyl;

$R^3$ represents $C_{1-3}$alkyl substituted by a phenyl group which may itself optionally be substituted by one or more of $C_{1-6}$alkyl, $C_{2-6}$alkenyl, $C_{2-6}$alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ and CONR$^c$R$^d$;

$R^4$ and $R^5$ each represent H, $C_{1-6}$alkyl or $C_{2-6}$alkenyl;

Z represents O or S;

$R^{12}$ represents H, $C_{1-6}$alkyl, phenyl (optionally substituted by one or more of $C_{1-6}$alkyl, $C_{1-6}$alkoxy, halo and trifluoromethyl) or phenyl($C_{1-4}$alkyl) (optionally substituted in the phenyl ring by one or more of $C_{1-6}$alkyl, $C_{1-6}$alkoxy, halo and trifluoromethyl);

$R^a$ and $R^b$ each independently represent H, $C_{1-6}$alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$alkyl, $C_{1-6}$alkoxy, halo and trifluoromethyl) or R$^a$ and R$^b$ together form a chain $(CH_2)_p$ optionally substituted by oxo where p is 4 or 5 and where one methylene group may optionally be replaced by an oxygen atom or a group NR$^x$, where R$^x$ is H or $C_{1-6}$alkyl;

$R^c$ and $R^d$ independently represent H, $C_{1-6}$alkyl, phenyl or trifluoromethyl; and Het represents an aromatic heterocycle optionally substituted by $C_{1-6}$alkyl, $C_{1-6}$alkoxy, oxo, thioxo, halo, trifluoromethyl, NR$^a$R$^b$, NR$^a$COR$^b$, CONR$^a$R$^b$, CO$_2$R$^a$, SR$^a$, SO$_2$R$^a$ or CH$_2$OR$^a$, where R$^a$ and R$^b$ are as above defined, with the exception of the compounds: 1-hydroxy-1-phenyl-2-benzyloxyethane; and 1-hydroxy-1-phenyl-2-(( 4-methoxyphenyl)methyloxy)ethane.

2. A compound as claimed in claim 1 of formula (IA):

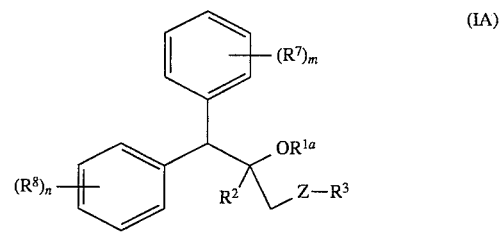

(IA)

wherein

Z, $R^2$ and $R^3$ are as defined for formula (I) above;

$R^{1a}$ represents H or $C_{1-6}$alkyl optionally substituted by hydroxy, cyano, COR$^a$, COOR$^a$, CONR$^a$R$^b$, COC$_{1-6}$alkylNR$^a$R$^b$, CONR$^{12}$C$_{1-6}$alkylOR$^a$, CONR$^{12}$C$_{1-6}$alkylCONR$^a$R$^b$ or NR$^a$R$^b$ (where R$^a$, R$^b$ and R$^{12}$ are as defined for formula (I) above); phenyl($C_{1-4}$alkyl) (optionally substituted by one or more of $C_{1-6}$alkyl, $C_{1-6}$alkoxy, halo and trifluoromethyl in the phenyl ring); $C_{2-6}$alkenyl; $C_{2-6}$alkynyl; COR$^a$; COOR$^a$; COC$_{1-6}$alkylhalo; COC$_{1-6}$alkylNR$^a$R$^b$; CONR$^{12}$C$_{1-6}$alkylCONR$^a$R$^b$; CONR$^a$R$^b$; or SO$_2$R$^a$; or R$^1$ and R$^2$ together form a chain $(CH_2)_q$ optionally substituted by oxo where q is 4 or 5 and where one methylene group may optionally be replaced by an oxygen atom or a group NR$^x$, where R$^x$ is H or $C_{1-6}$ alkyl;

each $R^7$ independently represents $C_{1-6}$alkyl, $C_{1-6}$alkoxy, halo or trifluoromethyl;

each $R^8$ independently represents $C_{1-6}$alkyl, $C_{1-6}$alkoxy, halo or trifluoromethyl; and n and m each represent 0, 1, 2 or 3; or a pharmaceutically acceptable salt or prodrug thereof.

3. A compound as claimed in claim 1 of formula (IB):

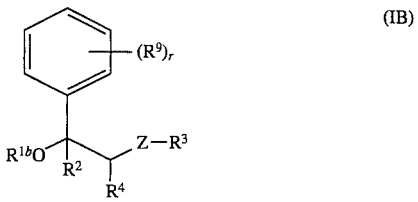

(IB)

wherein Z, $R^3$ and $R^4$ are as defined for formula (I) above;

$R^{1b}$ represents: H;

$C_{1-6}$alkyl optionally substituted by hydroxy, cyano, COR$^a$, COOR$^a$, CONR$^a$R$^b$, COC$_{1-6}$alkylNR$^a$R$^b$, CONR$^{12}$C$_{1-6}$alkylOR$^a$, Het; COHet; CONR$^{12}$C$_{1-6}$alkylCONR$^a$R$^b$ or NR$^a$R$^b$;

phenyl($C_{1-4}$alkyl) (optionally substituted by one or more of $C_{1-6}$alkyl, $C_{1-6}$ alkoxy, halo and trifluoromethyl in the phenyl ring);

$C_{2-6}$ alkenyl;

$C_{2-6}$ alkynyl;

COR$^a$;

COOR$^a$;

COHet;

COC$_{1-6}$alkylhalo;

COC$_{1-6}$alkylNR$^a$R$^b$;

CONR$^{12}$C$_{1-6}$alkylCONR$^a$R$^b$;

CONR$^a$R$^b$; or

SO$_2$R$^a$;

where R$^a$, R$^b$ and R$^{12}$ are as defined for formula (I) above;

$R^2$ represents H, $C_{1-6}$alkyl or $C_{2-6}$alkenyl;

each $R^9$ independently represents $C_{1-6}$alkyl, $C_{1-6}$alkoxy, halo or trifluoromethyl;

r represents 0, 1, 2 or 3; and

Het represents an aromatic heterocycle optionally substituted by $C_{1-6}$alkyl, $C_{1-6}$alkoxy, oxo, thioxo, halo, trifluoromethyl $NR^aR^b$, $NR^aCOR^b$, $CONR^aR^b$, $CO_2R^a$, $SR^a$, $SO_2R^a$ or $CH_2OR^a$, where $R^a$ and $R^b$ are as above defined; or a salt or prodrug thereof; with the exception of the compounds:

1-hydroxy-1-phenyl-2-benzyloxyethane; and
1-hydroxy-1-phenyl-2-(4-methoxyphenyl)methyloxyethane.

4. A compound as claimed in claim 1 wherein Q is optionally substituted benzhydryl.

5. A compound as claimed in claim 1 wherein Q is optionally substituted phenyl.

6. A compound as claimed in claim 1, wherein $R^1$ represents H or $C_{1-4}$alkyl substituted by $CONR^aR^b$, $COOR^a$ or $CONR^{12}C_{1-6}$alkylHet.

7. A compound as claimed in claim 1 wherein $R^3$ represents $C_{1-3}$alkyl substituted by a phenyl group, which phenyl group is substituted by one or two substituents selected from $C_{1-4}$alkyl, $C_{1-4}$alkoxy, trifluoromethyl and halo.

8. A compound as claimed in any claim 1 wherein Z is O.

9. A compound as claimed in claim 1 selected from:
1-(3,5-bis(trifluoromethyl)phenyl)methyloxy-3,3-diphenyl-2-hydroxypropane;
1-(3,5-bis(trifluoromethyl)phenyl)methyloxy-2-(carboxamidomethyloxy)- 3,3-diphenylpropane;
2-(3,5-bis(trifluoromethyl)phenyl)methyloxy-1-phenylethanol;
1-(3,5-bis(trifluoromethyl)phenyl)methyloxy-2-[N-methyl-N-( 3-pyridylmethyl)acetamidomethyloxy]-2-phenylethane;
1-(3,5-bis(trifluoromethyl)phenyl)methyloxy-2-carbomethoxymethyloxy- 2-phenylethane;
1-(3,5-bis(trifluoromethyl)phenyl)methyloxy-2-N-methylcarboxamidomethyloxy- 2-phenylethane;
and pharmaceutically acceptable salts and prodrugs thereof.

10. A pharmaceutical composition comprising a compound of formula (I), or a salt or prodrug thereof

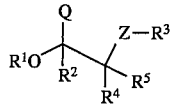
(I)

wherein

Q represents optionally substituted phenyl or optionally substituted benzhydryl;

$R^1$ represents: H;

$C_{1-6}$alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$; Het; COHet; $CONR^{12}C_{1-6}$alkylHet; $CONR^{12}C_{1-6}$alkyl$CONR^aR^b$ or $NR^aR^b$;

phenyl($C_{1-4}$alkyl) (optionally substituted by one or more of $C_{1-6}$alkyl, $C_{1-6}$alkoxy, halo and trifluoromethyl in the phenyl ring);

$C_{2-6}$alkenyl;

$C_{2-6}$alkynyl;

$COR^a$;

$COOR^a$;

COHet;

$COC_{1-6}$alkylhalo;

$COC_{1-6}$alkyl$NR^aR^b$;

$CONR^{12}C_{1-6}$alkyl$CONR^aR^b$;

$CONR^aR^b$; or $SO_2R^a$;

$R^2$ represents H, $C_{1-6}$alkyl or $C_{2-6}$alkenyl;

or $R^1$ and $R^2$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$alkyl;

$R^3$ represents $C_{1-3}$alkyl substituted by a phenyl group which may itself optionally be substituted by one or more of $C_{1-6}$alkyl, $C_{2-6}$alkenyl, $C_{2-6}$alkynyl, halo, cyano nitro, trifluoromethyl, trimethylsilyl, , $SR^c$, $SOR^c$, $SO_2R^c$, $OR^c$, $NR^cR^d$, $NR^cCOR^d$, $NR^cCOOR^d$, $COOR^c$ and $CONR^cR^d$;

$R^4$ and $R^5$ each represent H, $C_{1-6}$alkyl or $C_{2-6}$alkenyl;

Z represents O or S;

$R^{12}$ represents H, $C_{1-6}$alkyl, phenyl (optionally substituted by one or more of $C_{1-6}$alkyl, $C_{1-6}$alkoxy, halo and trifluoromethyl) or phenyl($C_{1-4}$alkyl) (optionally substituted in the phenyl ring by one or more of $C_{1-6}$alkyl, $C_{1-6}$alkoxy, halo and trifluoromethyl);

$R^a$ and $R^b$ each independently represent H, $C_{1-6}$ alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$alkyl, $C_{1-6}$alkoxy, halo and trifluoromethyl) or $R^a$ and $R^b$ together form a chain $(CH_2)_p$ optionally substituted by oxo where p is 4 or 5 and where one methylene group may optionally be replaced by an oxygen atom or a group $NR^x$, where $R^x$ is H or $C_{1-6}$ alkyl;

$R^c$ and $R^d$ independently represent H, $C_{1-6}$alkyl, phenyl or trifluoromethyl; and Het represents an aromatic heterocycle optionally substituted by $C_{1-6}$alkyl, $C_{1-6}$alkoxy, oxo, thioxo, halo, trifluoromethyl, $NR^aR^b$, $NR^aCOR^b$, $CONR^aR^b$, $CO_2R^a$, $SR^a$, $SO_2R^a$, or $CH_2OR^a$, where $R^a$ and $R^b$ are as above defined;

in association with a pharmaceutically acceptable carrier.

11. A method for the treatment of a physiological disorder associated with an excess of tachykinins, which method comprises administration to a patient in need thereof of a tachykinin-reducing amount of a compound of formula (I), or a salt or prodrug thereof

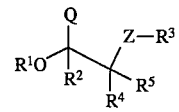
(I)

wherein

Q represents optionally substituted phenyl or optionally substituted benzhydryl;

$R^1$ represents: H;

$C_{1-6}$alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$; Het; COHet; $CONR^{12}C_{1-6}$alkylHet; $CONR^{12}C_{1-6}$alkyl$CONR^aR^b$ or $NR^aR^b$;

phenyl($C_{1-4}$alkyl) (optionally substituted by one or more of $C_{1-6}$alkyl, $C_{1-6}$alkoxy, halo and trifluoromethyl in the phenyl ring);

$C_{2-6}$alkenyl;

$C_{2-6}$alkynyl;

$COR^a$;

$COOR^a$;

COHet;
COC$_{1-6}$alkylhalo;
COC$_{1-6}$alkylNR$^a$R$^b$;
CONR$^{12}$C$_{1-6}$alkylCONR$^a$R$^b$;
CONR$^a$R$^b$; or
SO$_2$R$^a$;

R$^2$ represents H, C$_{1-6}$alkyl or C$_{2-6}$alkenyl;

or R$^1$ and R$^2$ together form a chain (CH$_2$)$_q$ optionally substituted by oxo where q is 4 or 5 and where one methylene group may optionally be replaced by an oxygen atom or a group NR$^x$, where R$^x$ is H or C$_{1-6}$alkyl;

R$^3$ represents C$_{1-3}$alkyl substituted by a phenyl group which may itself optionally be substituted by one or more of C$_{1-6}$alkyl, C$_{2-6}$alkenyl, C$_{2-6}$alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ and CONR$^c$R$^d$;

R$^4$ and R$^5$ each represent H, C$_{1-6}$alkyl or C$_{2-6}$alkenyl;

Z represents O or S;

R$^{12}$ represents H, C$_{1-6}$alkyl, phenyl (optionally substituted by one or more of C$_{1-6}$alkyl, C$_{1-6}$alkoxy, halo and trifluoromethyl) or phenyl(C$_{1-4}$alkyl) (optionally substituted in the phenyl ring by one or more of C$_{1-6}$alkyl, C$_{1-6}$alkoxy, halo and trifluoromethyl);

R$^a$ and R$^b$ each independently represent H, C$_{1-6}$ alkyl, phenyl (optionally substituted by one or more of C$_{1-6}$alkyl, C$_{1-6}$alkoxy, halo and trifluoromethyl), phenyl(C$_{1-4}$alkyl) (optionally substituted in the phenyl ring by one or more of C$_{1-6}$alkyl, C$_{1-6}$alkoxy, halo and trifluoromethyl) or R$^a$ and R$^b$ together form a chain (CH$_2$)$_p$ optionally substituted by oxo where p is 4 or 5 and where one methylene group may optionally be replaced by an oxygen atom or a group NR$^x$, where R$^x$ is H or C$_{1-6}$ alkyl;

R$^c$ and R$^d$ independently represent H, C$_{1-6}$alkyl, phenyl or trifluoromethyl; and Het represents an aromatic heterocycle optionally substituted by C$_{1-6}$alkyl, C$_{1-6}$alkoxy, oxo, thioxo, halo, trifluoromethyl, NR$^a$R$^b$, NR$^a$COR$^b$, CONR$^a$R$^b$, CO$_2$R$^a$, SR$^a$, SO$_2$R$^a$ or CH$_2$OR$^a$, where R$^a$ and R$^b$ are as above defined.

12. A method according to claim 11 for the treatment of pain or inflammation.

13. A method according to claim 11 for the treatment of migraine.

14. A method according to claim 11 for the treatment of arthritis.

* * * * *